(12) United States Patent  (10) Patent No.: US 9,055,950 B2
Beani et al.  (45) Date of Patent: Jun. 16, 2015

(54) METHOD AND SYSTEM FOR DELIVERING A TISSUE TREATMENT USING A BALLOON-CATHETER SYSTEM

(71) Applicants: Florent Beani, Gex (FR); Guillaume Herry, Lausanne (CH); Saoussene Sadoun, Neuilly plaisance (FR); Philippe Perrin, Paris (FR); Cecile Boyer-Joubert, Fontenay aux Roses (FR)

(72) Inventors: Florent Beani, Gex (FR); Guillaume Herry, Lausanne (CH); Saoussene Sadoun, Neuilly plaisance (FR); Philippe Perrin, Paris (FR); Cecile Boyer-Joubert, Fontenay aux Roses (FR)

(73) Assignee: CHEMO S.A. FRANCE, Sevres (FR)

( * ) Notice: Subject to any disclaimer, the term of this patent is extended or adjusted under 35 U.S.C. 154(b) by 154 days.

(21) Appl. No.: 13/842,648

(22) Filed: Mar. 15, 2013

(65) Prior Publication Data

US 2014/0276781 A1 Sep. 18, 2014

(51) Int. Cl.
*A61B 18/18* (2006.01)
*A61B 18/14* (2006.01)
*A61B 17/42* (2006.01)
*A61B 18/00* (2006.01)

(52) U.S. Cl.
CPC ............... *A61B 18/14* (2013.01); *A61B 17/42* (2013.01); *A61B 18/1485* (2013.01); *A61B 2018/0022* (2013.01); *A61B 2018/00559* (2013.01); *A61B 2018/00791* (2013.01); *A61B 2018/00875* (2013.01)

(58) Field of Classification Search
USPC .......................................................... 606/41
See application file for complete search history.

(56) References Cited

U.S. PATENT DOCUMENTS

| | | |
|---|---|---|
| 5,505,730 A | 4/1996 | Edwards |
| 5,575,788 A | 11/1996 | Baker et al. |
| 5,713,942 A | 2/1998 | Stern et al. |
| 5,848,969 A | 12/1998 | Panescu et al. |
| 5,879,347 A | 3/1999 | Saadat |
| 5,891,134 A | 4/1999 | Goble et al. |
| 5,904,651 A | 5/1999 | Swanson et al. |

(Continued)

FOREIGN PATENT DOCUMENTS

WO 2013022853 A1 2/2013

OTHER PUBLICATIONS

International Search Report and Written Opinion of the International Searching Authority in application No. PCT/IB/2014/059720, dated Jul. 11, 2014.

*Primary Examiner* — Robert N Wieland
(74) *Attorney, Agent, or Firm* — Don J. Pelto, Esq.; Sheppard, Mullin, Richter & Hampton LLP

(57) ABSTRACT

A balloon catheter system configured to deliver one or more stimulation signal to a tissue comprises an expandable balloon disposed around a distal portion of a catheter, a plurality of electrodes, and an external sheath having a lumen sized to slidably accommodate the expandable balloon, catheter and the plurality of electrodes. The plurality of electrodes are flexibly distributed along a balloon length and are configured to deliver the stimulation signals to the tissue. The plurality of electrodes may preferably be disposed on a flexible frame coupled externally of the expandable balloon and in sliding engagement to the balloon during inflation and deflation. The flexible frame may further comprise one or more sensors. The external sheath is made of a non-conductive material and is configured to prevent delivery of the stimulation signals by the electrodes disposed along an inoperable length of the expandable balloon when the balloon is inflated.

25 Claims, 7 Drawing Sheets

(56) References Cited

U.S. PATENT DOCUMENTS

| | | |
|---|---|---|
| 6,024,740 A | 2/2000 | Lesh et al. |
| 6,123,718 A | 9/2000 | Tu et al. |
| 6,179,832 B1 | 1/2001 | Jones et al. |
| 6,254,599 B1 | 7/2001 | Lesh et al. |
| 6,425,877 B1 | 7/2002 | Edwards |
| 6,500,174 B1 | 12/2002 | Maguire et al. |
| 6,554,780 B1 | 4/2003 | Sampson et al. |
| 6,752,805 B2 | 6/2004 | Maguire et al. |
| 6,813,520 B2 | 11/2004 | Truckai et al. |
| 6,881,213 B2 | 4/2005 | Ryan et al. |
| 7,150,745 B2 | 12/2006 | Stern et al. |
| 7,371,231 B2 | 5/2008 | Rioux et al. |
| 7,689,290 B2 | 3/2010 | Ingle et al. |
| 8,097,926 B2 | 1/2012 | De Graff et al. |
| 8,192,426 B2 | 6/2012 | Stern et al. |
| 8,353,908 B2 | 1/2013 | Edwards et al. |
| 8,364,237 B2 | 1/2013 | Stone et al. |
| 8,382,753 B2 | 2/2013 | Truckai |
| 8,394,037 B2 | 3/2013 | Toth |
| 8,396,548 B2 | 3/2013 | Perry et al. |
| 8,401,667 B2 | 3/2013 | Gustus et al. |
| 2002/0022870 A1 | 2/2002 | Truckai et al. |
| 2008/0125772 A1 | 5/2008 | Stone et al. |
| 2008/0262489 A1 | 10/2008 | Steinke |
| 2010/0049190 A1 | 2/2010 | Long et al. |
| 2010/0204560 A1 | 8/2010 | Salahieh et al. |
| 2010/0217250 A1 | 8/2010 | Sampson |
| 2010/0228239 A1 | 9/2010 | Freed |
| 2011/0130708 A1 | 6/2011 | Perry et al. |
| 2011/0306904 A1 | 12/2011 | Jacobson et al. |
| 2012/0059368 A1 | 3/2012 | Takaoka et al. |
| 2012/0101413 A1 | 4/2012 | Beetel et al. |
| 2012/0116384 A1 | 5/2012 | Truckai |
| 2012/0220996 A1* | 8/2012 | Stern et al. .............. 606/33 |
| 2013/0085493 A1 | 4/2013 | Bloom et al. |

\* cited by examiner

Measure Uterus Length

Dilate Cervix

Evaluate Cervix Length

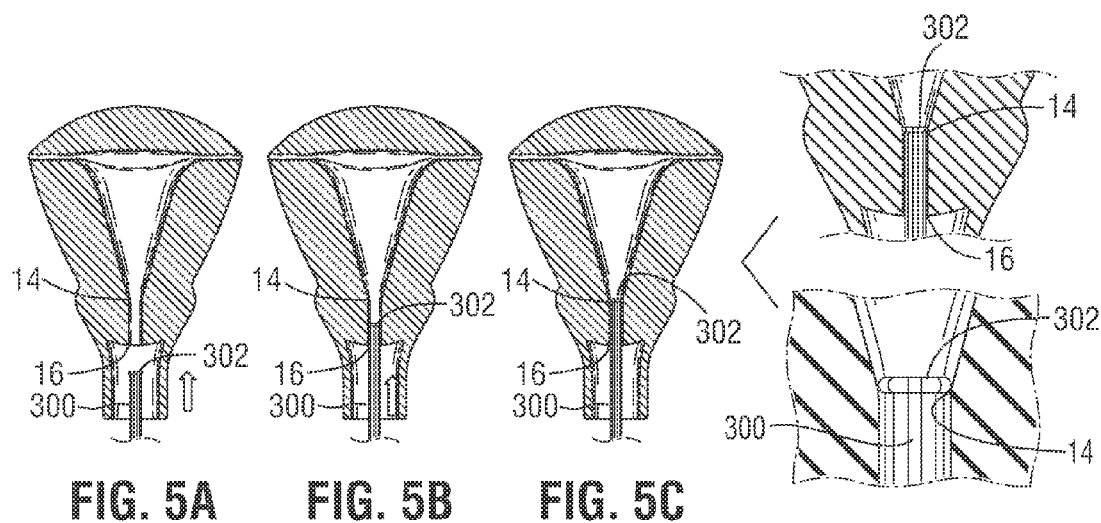
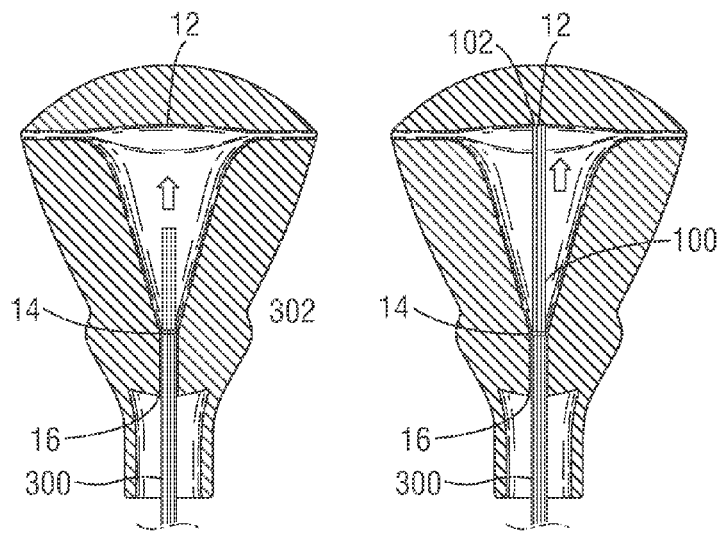

METHOD AND SYSTEM FOR DELIVERING A TISSUE TREATMENT USING A BALLOON-CATHETER SYSTEM

FIELD OF THE INVENTION

The field of the invention is directed generally to a method and apparatus for delivering a tissue treatment using a balloon catheter system.

BACKGROUND

There are a variety of treatment modalities that may be delivered to treat a diseased tissue. Endometrial ablation, for example, is a medical procedure that is used to remove (ablate) or destroy the endometrial lining of a uterus. This technique is most often employed to treat women who suffer from excessive or prolonged bleeding during their menstrual cycle and who either cannot or do not wish to undergo a hysterectomy. Such heavy menstrual bleeding is most commonly due to dysfunctional uterine bleeding or adenomyosis.

There are a number of challenges to delivering treatment to tissue that is located within body cavities and lumens which are not easily accessible to the physician. Moreover, it is often difficult to deliver the appropriate treatment to the entirety of the tissue surface due to irregular convolutions and contouring of the tissue surface. This difficulty is further compounded by fact that each patient presents his or her own unique anatomical features and differences, that a one size fits all approach cannot be employed and the treatment or delivery system must be customized to accommodate the patient's unique anatomy.

BRIEF SUMMARY

The balloon catheter systems disclosed herein provide a mechanism to adjust and control the operable portions or dimensions of the balloon and associated electrodes which deliver one or more stimulating signals to the target tissue. One advantage of the balloon catheter system disclosed herein is the ability to conform the shape and size of the balloon and electrodes to the tissue surface, such as the uterine cavity, thereby bringing electrodes into contact with the endometrium and thus allowing an improved delivery of stimulating signals, such as an RF current, to ablate the tissue. Another advantage is that it permits the physician or operator to control and protect certain tissue regions for which the delivery of a stimulating signal is undesired.

In one preferred embodiment, a balloon catheter system configured to deliver a stimulation signal to a tissue is provided. The system comprises an expandable and extensible balloon, a plurality of electrodes distributed along a balloon length configured to deliver one or more stimulating signals, and a sheath having a lumen configured to slidably accommodate the balloon and the plurality of electrodes and to maintain portions of the balloon and the plurality of electrodes along an inoperable portion of the balloon length compressed within the lumen when the balloon is inflated. The plurality of electrodes are sufficiently flexible such when the balloon is inflated, the plurality of electrodes contacting the tissue conforms to the contours of the tissue. The sheath blocks or prevents stimulating signals from the plurality of electrodes disposed along the inoperable portion from reaching the surrounding tissue.

In accordance with a first aspect, the sheath is configured to permit exposed portions of the balloon and plurality of electrodes along an operable portion of the balloon length to expand and directly contact the surrounding tissue when the expandable balloon is inflated.

In accordance with a second aspect, the plurality of electrodes are electrically coupled via interconnects that are stretchable, flexible, or both.

In accordance with a third aspect, the plurality of electrodes comprise one or a combination of unipolar and multipolar electrodes.

In accordance with a fourth aspect, the plurality of electrodes are disposed on a flexible conductive ribbon, such as a flexible printed circuit, and the conductive ribbon is disposed radially around a peripheral surface of the balloon.

In accordance with a fifth aspect, the plurality of electrodes are disposed on a flexible frame externally of the balloon. The flexible frame may be disposed in sliding engagement to the balloon during inflation and deflation. The flexible frame may further comprise one or more sensors.

In accordance with a sixth aspect, the balloon is made of an elastomeric material and the plurality of electrodes are encapsulated within the elastomeric material.

In accordance with a seventh aspect, the plurality of electrodes may be disposed on an external and/or an internal surface of the balloon.

In another preferred embodiment, a balloon catheter system configured to deliver a stimulation signal to a tissue is provided. The system comprises a catheter, an expandable balloon disposed around a distal portion of the catheter and having a balloon length, a plurality of electrodes configured to deliver one or more stimulation signals to the tissue, and an external sheath made of a non-conductive material. The electrodes are flexibly distributed along the balloon length. The external sheath comprises a lumen sized to slidably accommodate the balloon, the plurality of electrodes and the catheter. The external sheath is configured to prevent delivery of the one or more stimulation signals by the electrodes disposed along an inoperable length of the balloon when the balloon is inflated.

In accordance with a first aspect, the external sheath comprises an open mouth and a curved lip peripherally of the open mouth from which the balloon is exposed.

In accordance with a second aspect, an operable length of the balloon is exposed from the external sheath and the electrodes disposed on the operable length directly contact, conform to and deliver stimulating signals to the surrounding tissue when the balloon is inflated.

In accordance with a third aspect, the one of more stimulation signals includes, but is not limited to, one or a combination of RF energy, cryoablation, laser energy, high-intensity focused ultrasound, high-voltage electrical stimulation and heat.

In accordance with a fourth aspect, the system further comprises one or more sensors disposed on the balloon to monitor one or a combination of parameters that includes, but is not limited to, tissue temperature, internal balloon pressure, contact, tissue impedance, and humidity.

In accordance with a fifth aspect, the plurality of electrodes are disposed on a flexible frame externally of the balloon. The flexible frame may be coupled in sliding engagement to the balloon during inflation and deflation. The flexible frame may further comprise one or more sensors.

In a further embodiment, a method of delivering one or more stimulation signals to an endometrium of a patient is provided. The method comprises positioning a sheath extending through the patient's cervix; introducing an expandable balloon into the uterus via a lumen of the sheath, the balloon comprising a plurality of electrodes distributed along a balloon length; positioning the balloon such that a top portion of the balloon contacts the fundus of the uterus; inflating the balloon such that operable portions of the peripheral surface of the balloon and the plurality of electrodes contact the patient's endometrium; and delivering one or more stimulation signals via the operable portion of the electrodes to the endometrium.

In accordance with a first aspect, the operable portions correspond to portions of the balloon and the plurality of electrodes exposed from the sheath.

In accordance with a second aspect, the method further comprises positioning the sheath such that a lip disposed on a distal end of the sheath is seated on the internal os of the cervix.

In accordance with a third aspect, the method further comprises maintaining inoperable portions of the balloon and the plurality of electrodes within the sheath during the inflating and delivering.

In accordance with a fourth aspect, the one or more stimulation signals is one or a combination that includes, but is not limited to, RF energy, cryoablation, laser energy, high-intensity focused ultrasound, high-voltage electrical stimulation, and heat.

In accordance with a fifth aspect, the method further comprises monitoring one or more parameters including, but not limited to, tissue temperature, internal balloon pressure, contact, tissue impedance, and humidity. The monitoring may be performed concurrently with either one or both of the inflating and the delivering.

Other objects, features and advantages of the described preferred embodiments will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

Preferred and non-limiting embodiments of the inventions may be more readily understood by referring to the accompanying drawings in which:

FIGS. 5A-5C depict the sequence of steps involved in introducing and positioning the sheath within the cervix.

FIGS. 6A-6B depict the sequence of steps involved in introducing and positioning the expandable balloon inside the uterus.

Like numerals refer to like parts throughout the several views of the drawings.

DETAILED DESCRIPTION OF THE PREFERRED EMBODIMENTS

Specific, non-limiting embodiments of the present invention will now be described with reference to the drawings. It should be understood that such embodiments are by way of example only and merely illustrative of but a small number of embodiments within the scope of the present invention. Various changes and modifications obvious to one skilled in the art to which the present invention pertains are deemed to be within the spirit, scope and contemplation of the present invention as further defined in the appended claims.

The methods and systems for delivering a tissue treatment using a balloon catheter described herein are useful particularly where it is desired to deliver a stimulating treatment to tissue having an uneven or undulating surface. While the balloon catheter systems are described herein in the context of delivering a stimulating signal to an endometrium, it is understood that the balloon catheter system is equally suitable in applications where a stimulating signal is desired to be applied to other types of tissue surfaces, tissue cavities or tissue lumens.

Figure 1:
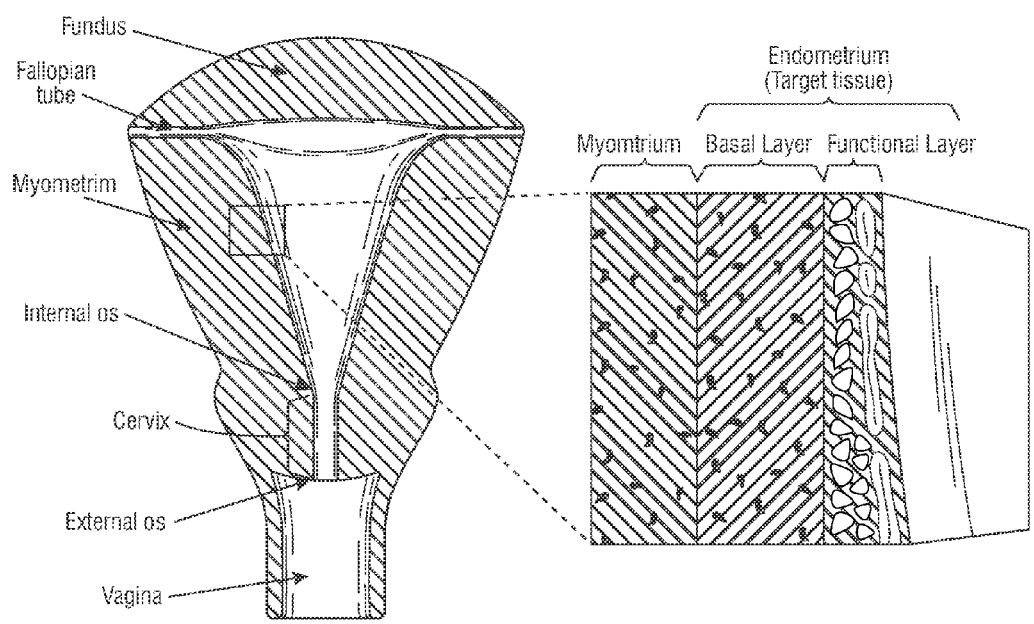
FIG. 1 illustrates the anatomical features that characterize a uterus.

FIG. 1 illustrates the significant anatomical features of the uterus. As can be seen, the uterus is shaped as an inverted triangle and the anatomical features pertinent to the operation of the balloon catheter systems described herein include the fundus, the cervix, which comprises a canal that is bounded by the external os and the internal os, and the uterine cavity which is lined by the endometrium. The length of the uterus is typically measured as the distance between the fundus and the internal os of the cervix.

Figure 2:
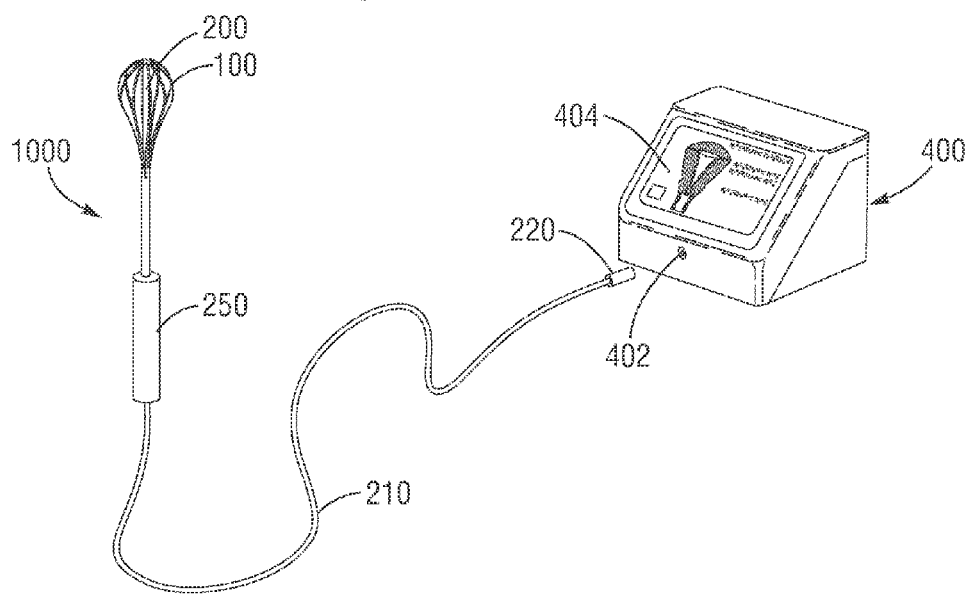
FIG. 2 depict the balloon catheter system together with an associated central control unit.

FIG. 2 illustrates a treatment delivery system 1000 comprising an expandable balloon 100 disposed around a distal portion of a flexible catheter 200. The balloon 100 is preferably expandable and extensible or stretchable along its length and width. Additionally, the balloon 100 may be designed for single use. A handle 250 is coupled to the distal and proximal catheter portions 200, 210 and the proximal catheter portion terminates in a plug 220 configured to be connected to a control unit 400 via a hybrid connector 402. The control unit 400 includes a user interface comprising a graphical display 404. The control unit 400 may be configured to perform a variety of functions, including controlling the inflation and deflation of the expandable balloon 100 via a fluid pump, delivering one or a combination of stimulation signals and receiving and monitoring signals from one or more sensors. Measured sensor parameters may include tissue temperature, internal balloon pressure, contact, tissue impedance, and humidity. The flexible catheter 200, 210 and the control unit 400 comprise a plurality of connections, including electrical input and output connections and power and fluid connections to pump and remove fluid into and from the expandable balloon 100. While the delivery system 1000 depicts a physical electrical connection between the catheter 200, 210 and the control unit 400, a wireless connection is also contemplated to be within the scope of the embodiments.

Figure 3A:
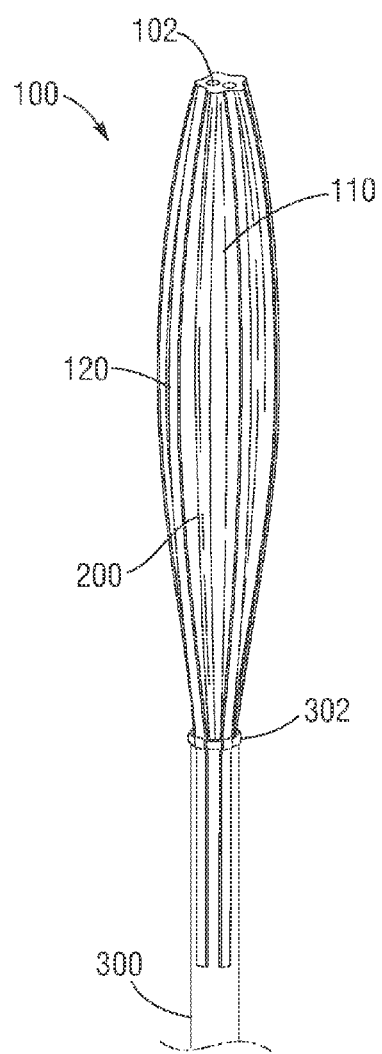
FIGS. 3A-3B are perspective views of the uninflated and inflated balloon, respectively.
Figure 3B:
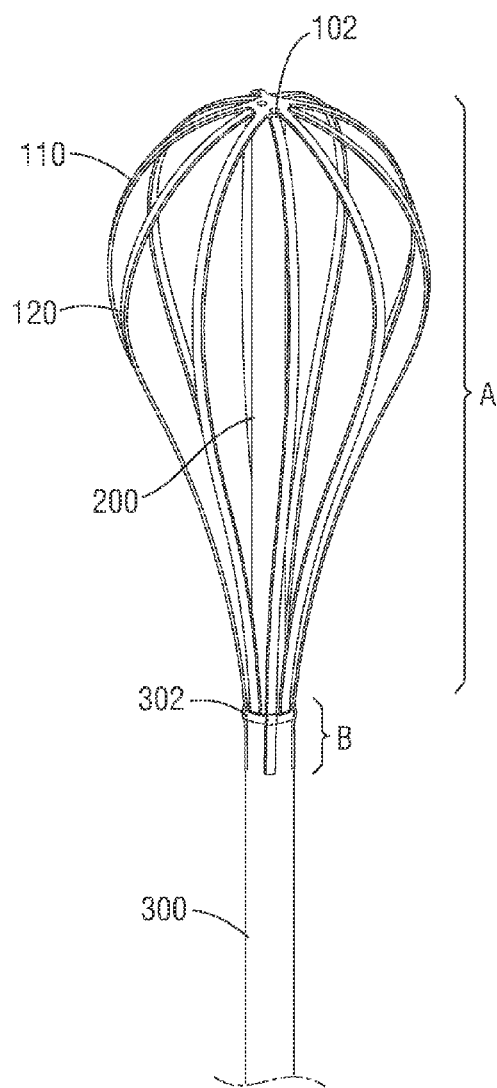

FIGS. 3A-3B depict the uninflated and inflated expandable balloons, respectively. The expandable balloon 100 is preferably made of an elastomeric material 110. In a preferred embodiment, the elastomeric surface 110 is resiliently biased to the uninflated and compressed state shown in FIG. 3A. The expandable balloon 100 inflates to an inflated state shown in FIG. 3B and readily conforms its shape in accordance to the contours of the volume within which it is constrained (e.g., a uterus). The inflation of the expandable balloon 100 is typically accomplished by delivering a controlled volume of fluid into the internal cavity of the expandable balloon 100 via the catheter 200. The fluid is preferably non-conductive and most preferably air.

The expandable balloon 100 comprises a top portion 102 that may further comprise one or more contact sensors. The contact sensors may cause an audible signal to be emitted or visual signal that may displayed on the graphical display 404 of the user interface upon contact of the one or more contact sensors with a tissue surface.

A plurality of electrodes 120 are flexibly distributed along a balloon length. In a preferred embodiment, the plurality of electrodes 120 are unipolar or multi-polar and are linearly coupled together via interconnects which are stretchable, flexible, or both.

In one embodiment, a flexible frame comprises the plurality of electrodes 120 to deliver the stimulating signals to the tissue and, optionally, a plurality of sensors to monitor at least one of a plurality of parameters. The flexible frame is disposed externally and slidably of the balloon 100 and may be provided in variety of patterns. The frame may be provided as a web covering the balloon 100 or a plurality of ribbons that extend radially or circumferentially between the distal and proximal ends of the balloon 100, as depicted in FIGS. 3A-3B.

In an alternative embodiment, the plurality of electrodes 120 are flexible and may be disposed on a flexible conductive ribbon that is disposed in a radial pattern from a top portion 102 of the expandable balloon 100. The fabrication and configuration of the flexible and/or stretchable electrodes 120 on the elastomeric surface 110 of the expandable balloon 100 are described in greater detail in U.S. Patent Pub. No. 2010/0298895, published Nov. 25, 2010, for "Systems, Methods, and Devices Using Stretchable or Flexible Electronics for Medical Applications" and U.S. Patent Pub. No. 2013/0041235, published Feb. 14, 2013, the entire contents of each of which are incorporated herein by reference in their entireties.

While the plurality of electrodes 120 are depicted as being disposed along an entire length of the balloon 100, it is understood that the plurality of electrodes 120 may be provided only along a portion of the entire length of the balloon 100. The distribution of the plurality of electrodes 120 may be configured based on the nature and type of the tissue to be targeted for treatment. For example, the distribution of the electrodes 120 may be concentrated in particular regions of the surface of the balloon 100 and more dispersed or absent on other portions of the surface of the balloon 100.

An external sheath 300 is provided to control the operable length of the expandable balloon 100 and therefore the operable length of the electrodes 120 that contacts and delivers treatment to the tissue surface within the body cavity when the expandable balloon 100 is inflated. FIG. 3B illustrates the balloon length as comprising an operable portion and exposed length A and an inoperable portion B that remains constrained within the external sheath 300. The external sheath 300 is preferably made of a material that is both electrically and thermally non-conductive so as to effectively block the stimulating signals from the electrodes disposed on the inoperable portion B contained within the sheath from reaching the adjacent tissues. A rounded lip 302 is provided at the distal end or mouth of the external sheath 300 so as to mitigate impingement and thus possible rupture of the elastomeric surface 110 when the expandable balloon 100 is inflated about its periphery.

The ability to adjust and vary the length of the expandable balloon 100 and thus the length of the electrodes 120 contacting the tissue is significant for at least two reasons. First, it permits the manufacture of a "one size fits all" expandable balloon that may be used in a variety of anatomical dimensions. Second, it permits the physician or the operator to control and protect certain tissue regions for which the delivery of a stimulating signal is undesired.

FIGS. 4-9 illustrate a use of the balloon catheter system 1000 for delivering an ablation energy, preferably a radio frequency (RF) current, to the endometrium. Such a treatment is desirable in patients suffering from dysfunction or excessive uterine bleeding or for whom ablation of the endometrium is desired. Because the dimensions of a female uterus is highly variable from patient to patient, the use of the balloon catheter system 1000 for delivering a treatment modality to the endometrium lining internal surface of the uterine cavity is illustrative of the utility of functions and features of the system.

Figures 4A, 4B, 4C:
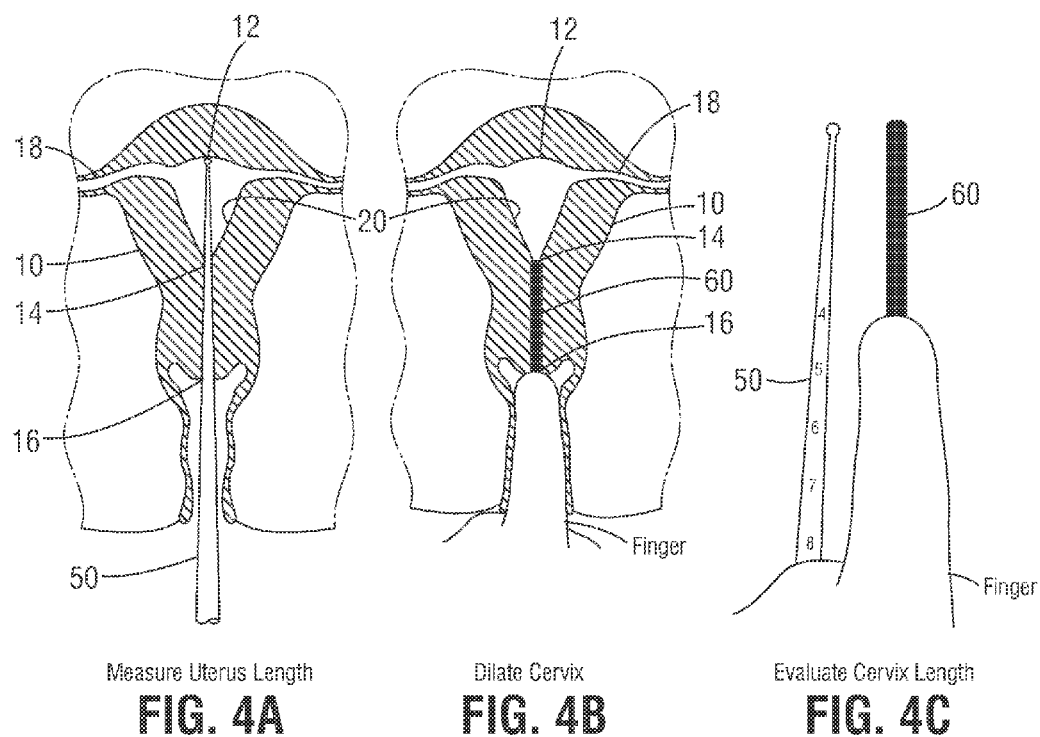
FIG. 4A-4C illustrates the steps of obtaining measurements of the lengths of the uterus and the cervix.

Prior art endometrium ablation devices have typically required information regarding the anatomical dimensions and features of the patient's uterus before selecting and initiating treatment. FIGS. 4A-4B illustrate the exemplary steps that are typically taken to determine both a uterus length and a cervical length.

As shown in FIG. 4A, a first measuring rod 50 having a rounded tip is inserted through the cervix and into the cavity of the uterus 10 until the rounded tip hits the fundus 12. A placeholder or a finger is then inserted into the vaginal canal to mark the location of the first measuring rod 50 at the external os 16 of the cervix. The measuring rod 50 typically comprises visible markings to show the units of measure.

As shown in FIG. 4B, a second measuring rod 60 is inserted into the cervix to the internal os 14. If necessary, the cervix is first dilated before insertion of the first and/or second measuring rods 50, 60. Again, a placeholder or a finger may be inserted into the vaginal canal to mark the location of the second measuring rod 60 at the external os 16 of the cervix.

As shown in FIG. 4C, the location of the placeholder or finger on the first and second measuring rods 50, 60 is compared to reveal both the lengths of the uterus the cervical canal bounded by the internal os 14 and the external os 16. More precisely, subtracting the marked length of the second measuring rod 60 from the marked length of the first measuring rod 50 reveals the length of the uterus (about 4 units), while the marked length of the second measuring rod 60 directly reveals the cervical length (about 4 units).

One advantage of using the balloon systems described herein is that it obviates the requirement to obtain precise anatomical measurements in order to deliver treatment. A single balloon catheter 100 is sized to accommodate a range of anatomical sizes and dimensions by controllable actuation of a protective sheath 300 relative to the balloon 100 to expose operable portions of the balloon 100.

FIGS. 5A-5C illustrate an exemplary method of inserting an external sheath 300 into and through the entire length of the cervical canal from the external os 16 to the internal os 14. The external sheath is first introduced into the vaginal canal and inserted into the cervix. Once the rounded lip 302 at the mouth of the external sheath 300 clears the internal os 14, the sheath 300 may be pulled back slightly to seat the rounded lip 302 on top of the internal os 14, as depicted in FIG. 5C.

FIGS. 6A-B show the introduction and positioning of the expandable balloon 100 in the uterine cavity. The expandable balloon 100 is inserted into the lumen of the external sheath 300 and emerges out of the rounded lip 302, as shown in FIG. 6A. It is also contemplated that the balloon 100 is provided in a compressed and assembled state within the external sheath 30 prior to use and that the balloon 100 need only be advanced out of the external sheath 300 once the external sheath 300 is positioned within the cervix.

As shown in FIG. 6B, the expandable balloon 100 is advanced upward (arrow) until the top portion 102 contacts the fundus 12. As previously indicated, one or more sensors may be provided at the top portion 102 to indicate when the top portion 102 has made physical contact with the fundus. Alternatively, whether or not contact has been made by the top portion 102 may be tactilely determined.

Once the expandable balloon 100 is properly positioned within the uterus (see FIG. 6B), operable portions of the balloon 100 and the electrodes 120 are provided to span substantially the entire length of the uterus, while inoperable portions of the balloon 100 and electrodes 120 are constrained and insulated from contacting the surrounding tissue by the external sheath 300. Here, the external sheath 300 functions to prevent the inoperable portions of the expandable balloon 100 from inflating within the cervix and also to prevent the stimulating signals from the inoperable portions of the electrodes 120 from being applied to the cervix. The length of the operable portions of the expandable balloon 100 and electrodes 120 is therefore tailored to the length of the patient's unique anatomy without the need for fabricating balloon catheters of different sizes.

Figure 7A:
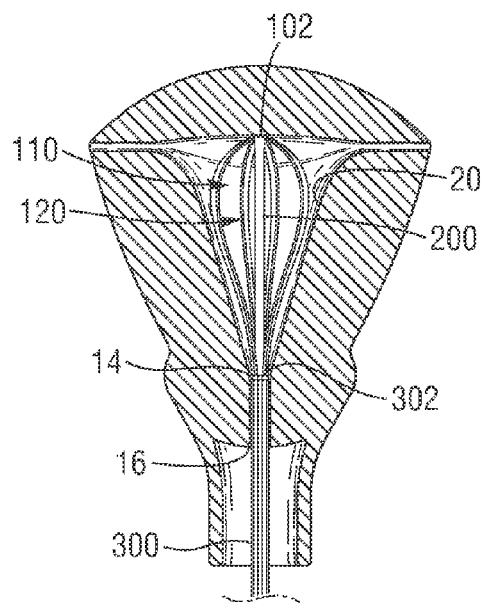
FIGS. 7A-7C depict the sequence of inflating the expandable balloon and delivering the treatment modality to the surrounding tissue.
Figure 7B:
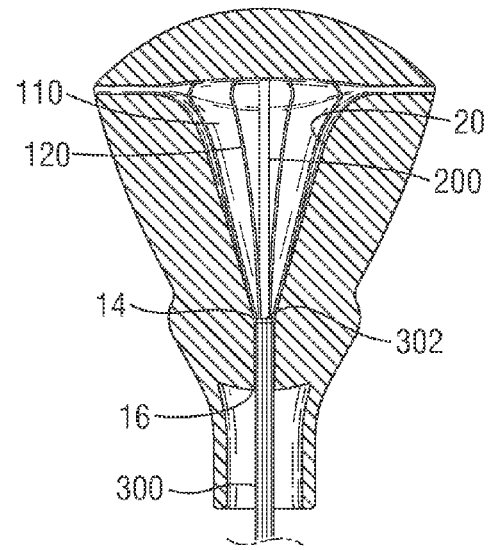
Figure 7C:
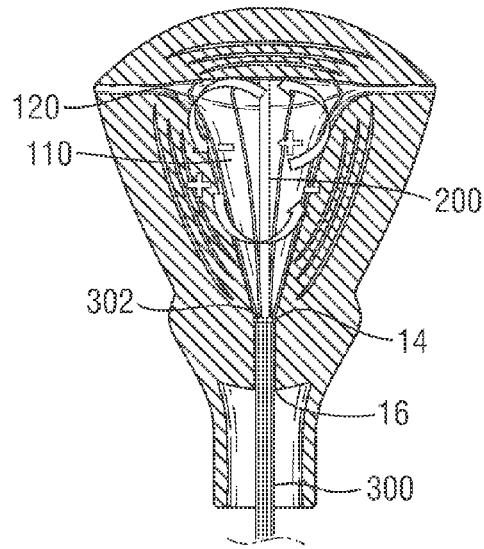

FIGS. 7A-7C illustrate the sequence of inflating the expandable balloon 100 and delivering the treatment modality or stimulating signals to the surrounding tissue. Again, the expandable balloon 100 inflates only along an operable length as demarcated by the mouth 302 of the external sheath 300.

The expandable balloon 100 inflates as the catheter delivers a fluid, preferably a non-conductive fluid (e.g., water, gas), into an internal cavity of the expandable balloon 100. In a preferred embodiment, the elastomeric surface 110 is extremely thin and extensible so as to promote deformation of the inflated balloon 100 such that it contacts a substantial, if not the entire, endometrial surface of the uterus, regardless its shape and size. This, in turn, ensures direct and contiguous contact by the plurality of electrodes 120 onto the tissue surface along its operable length.

Thus, even where the tissue surface takes on a dimension that is substantially different from the natural shape of the expandable balloon 100, the elastomeric surface 110 and the plurality of electrodes 120 is sufficiently flexible and/or stretchable to adapt to the volume and dimensions defined by the tissue surface. As shown in FIG. 7B, the naturally elongated spherical shape of the expandable balloon 100 adapts to the substantially triangular shape defined by the endometrium such that a substantial, if not the entire area of the endometrium is contacted by either the elastomeric surface 110 and/or the electrodes 120. Once the expandable balloon 100 is fully inflated and an operable length of the electrodes 120 are in contact with the tissue surface, one or more stimulating signals may be delivered to the tissue The pressure in the balloon will allow it to conform both in size and shape to the uterine cavity in a soft and conformal manner. This contact between the balloon 100 and endometrium brings the electrodes 120 into contact with the endometrium, thereby allowing an optimal heat delivery to the endometrium to be ablated.

Several types of stimulating signals may be applied, including unipolar RF energy, multi-polar RF energy, or multi-bipolar RF energy. Multi-polar electrodes have the advantage of delivering a more contiguous RF energy without gaps over unipolar electrodes.

Figure 8A:
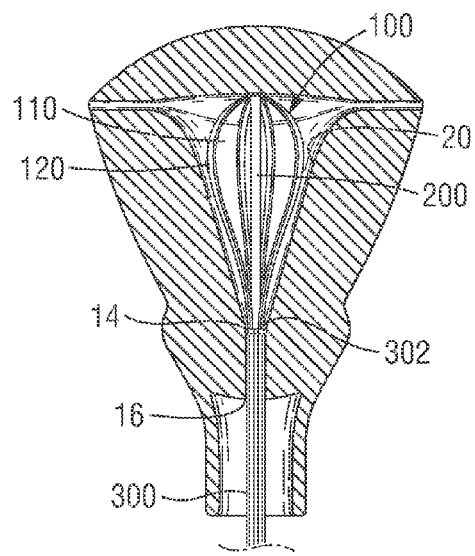
FIGS. 8A-8D depict the sequence of removing the expandable balloon and the sheath from the patient.
Figure 8B:
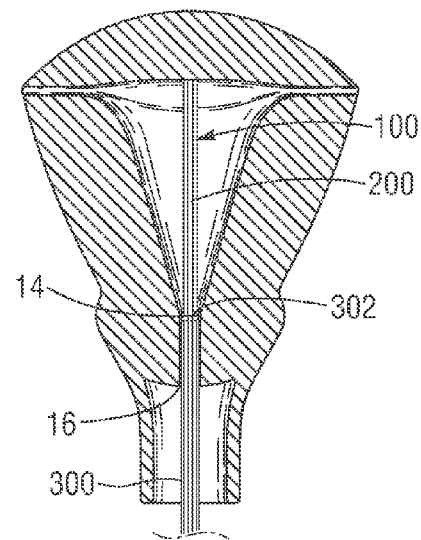
Figure 8C:
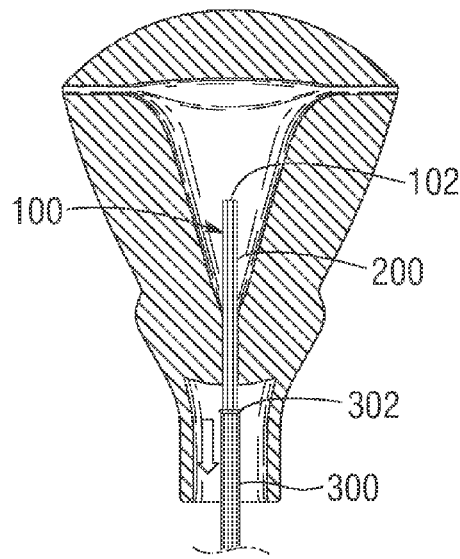
Figure 8D:
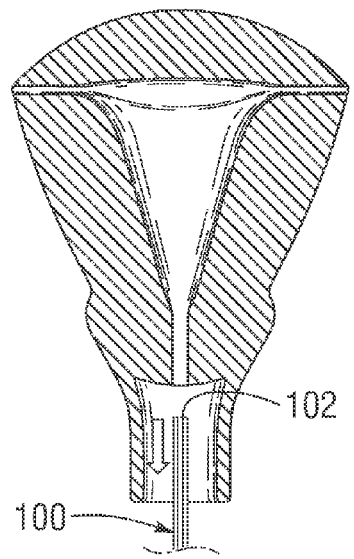

After treatment of the tissue is completed, the fluid inside the inflatable balloon 100 may be removed via vacuum suction or fluid exhaust (FIG. 8A) and the expandable balloon 100 and the plurality of electrodes 120 resiliently return to their uninflated initial state (FIG. 8B). The expandable balloon 100, electrodes 120, catheter 200 and external sheath 300 is then removed from the cervix canal (FIGS. 8C-8D). It is understood that the expandable balloon 100, electrodes 120 and catheter 200 may slide into the sheath 300 and be removed together with the sheath 300 from the uterus and cervix or that the expandable balloon 100, electrodes 120 and catheter 200 may first be removed entirely from the uterus and sheath 300 and that the sheath 300 may subsequently be removed from the cervix.

Figure 9:
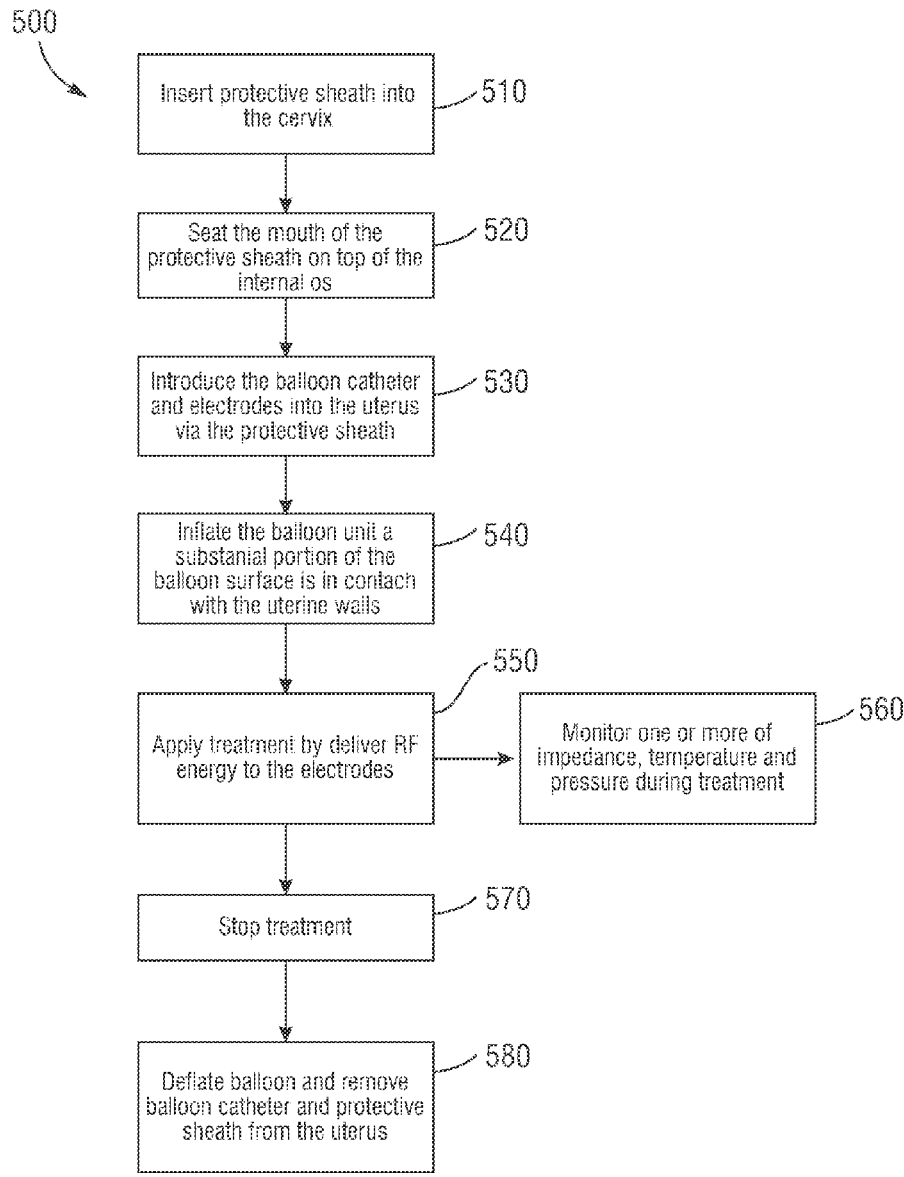
FIG. 9 is a flow chart depicting the exemplary steps in ablating the endometrium of a patient's uterus.

FIG. 9 summarizes an exemplary method 500 for treating the endometrium via RF ablation. A protective sheath is inserted into the cervix, either separately from or together with the balloon catheter and plurality of electrodes at 510. The protective sheath is provided to protect the tissue surrounding the cervical canal. The mouth of the protective sheath is seated on top of the internal os at 520 to complete the positioning of the protective sheath.

The balloon catheter together with the plurality of electrodes is introduced and positioned within the uterus via the protective sheath at 530. As previously described, the balloon catheter is provided in a single size (e.g., "one size fits all") and may be adapted to a number of different lengths and dimensions by virtue of the sliding engagement of the protective sheath around the balloon and electrodes. In a preferred embodiment, operable length of the balloon may be adjusted between 40 mm to 120 mm via the protective sheath. The protective sheath permits the use of a balloon catheter that is longer than the uterus (as measured from the fundus to the internal os), as the protective sheath may adjustably limit the operable length of the inflated balloon and thus the operable length of the electrodes applied to the tissue.

The balloon is then inflated until the operable portion of the balloon and the electrodes contact a substantial portion, if not the entire portion, of the target tissue or endometrium at 540. Once contact is made, the electrodes may deliver one or more stimulating signals to the endometrium at 550. In a preferred embodiment, an RF current is delivered having a frequency that is sufficient to produce necrosis of the tissue with a minimal value of 10 kHz to about several hundred kHz. In a preferred embodiment, the frequency of the RF current delivered to the endometrium is in the range of about 450 kHz to 500 kHz. As the electrical tissue conductivity may be modified considerably during heating, the RF current may be delivered in a pulsed manner. Optionally, a cooling mechanism may be provided to protect the electrodes from overheating. The target temperature to which the tissue is heated is in the range of 50 to 100 degrees Celsius, preferably above 60 degrees Celsius. The duration of the thermal ablation treatment is in the range of less than 10 minutes and, more preferably, less than 5 minutes, and more preferably about 1 minute.

Concurrently or thereafter, one or more of impedance, tissue temperature and balloon pressure may be monitored by sensors disposed on the balloon at 560. After less than 5 minutes, the treatment is terminated at 570. As a final step, the balloon is deflated the balloon, the electrodes and protective sheath are removed from the patient's body at 580.

The invention described and claimed herein is not to be limited in scope by the specific preferred embodiments disclosed herein, as these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

What is claimed is:

1. A balloon catheter system configured to deliver a stimulation signal to a tissue comprising:
   an expandable balloon;
   a plurality of electrodes distributed along a balloon length, the plurality of electrodes being sufficiently flexible such when the balloon is inflated, the plurality of electrodes contacting the tissue conforms to the contours of the tissue; and
   a sheath having a lumen configured to slidably accommodate the balloon and the plurality of electrodes and to maintain portions of the balloon and the plurality of electrodes along an inoperable portion of the balloon length compressed within the lumen when the balloon is inflated.

2. The balloon catheter of claim 1, wherein the sheath is configured to permit exposed portions of the balloon and plurality of electrodes along an operable portion of the balloon length to expand when the expandable balloon is inflated.

3. The balloon catheter of claim 1, wherein the plurality of electrodes are electrically coupled via interconnects that are stretchable, flexible, or both.

4. The balloon catheter of claim 1, wherein the plurality of electrodes comprise one or a combination of unipolar and multi-polar electrodes.

5. The balloon catheter of claim 1, wherein the plurality of electrodes are disposed on a flexible conductive ribbon and wherein the ribbon is disposed radially around a peripheral surface of the balloon.

6. The balloon catheter of claim 1, wherein the plurality of electrodes are disposed on a flexible frame externally of the balloon.

7. The balloon catheter of claim 6, the flexible frame further comprises one or more sensors.

8. The balloon catheter of claim 6, wherein the flexible frame is coupled in sliding engagement to the balloon during inflation and deflation.

9. The balloon catheter of claim 1, wherein the balloon is made of an elastomeric material and wherein the plurality of electrodes are encapsulated within the elastomeric material.

10. The balloon catheter of claim 1, wherein the plurality of electrodes are disposed either on an external or an internal surface of the balloon.

11. A balloon catheter system configured to deliver a stimulation signal to a tissue comprising:
    a catheter;
    an expandable balloon disposed around a distal portion of the catheter and having a balloon length;
    a plurality of electrodes configured to deliver one or more stimulation signals to the tissue, the electrodes being flexibly distributed along the balloon length; and
    an external sheath made of a non-conductive material, the external sheath having a lumen sized to slidably accommodate the balloon, the plurality of electrodes and the catheter and the external sheath being configured to prevent delivery of the one or more stimulation signals by the electrodes disposed along an inoperable length of the balloon when the balloon is inflated.

12. The balloon catheter of claim 11, wherein the external sheath comprises an open mouth and a curved lip peripherally of the open mouth from which the balloon is exposed.

13. The balloon catheter of claim 11, wherein an operable length of the balloon is exposed from the external sheath and wherein the electrodes disposed on the operable length directly contact, conform to and deliver stimulating signals to the surrounding tissue when the balloon is inflated.

14. The balloon catheter of claim 11, wherein the one of more stimulation signals is one or a combination of RF energy, cryoablation, laser energy, high-intensity focused ultrasound, high-voltage electrical stimulation and heat.

15. The balloon catheter of claim 11, further comprising one or more sensors disposed on the balloon to monitor one or a combination of parameters selected from the group consisting of: tissue temperature, internal balloon pressure, contact, tissue impedance, and humidity.

16. The balloon catheter of claim 11, wherein the plurality of electrodes are disposed on a flexible frame externally of the balloon.

17. The balloon catheter of claim 16, the flexible frame further comprising one or more sensors.

18. The balloon catheter of claim 16, wherein the flexible frame is coupled in sliding engagement to the balloon during inflation and deflation.

19. A method of delivering one or more stimulation signals to an endometrium of a patient, the method comprising:
    positioning a sheath extending through the patient's cervix;
    introducing an expandable balloon into the uterus via a lumen of the sheath, the balloon comprising a plurality of electrodes distributed along a balloon length;
    positioning the balloon such that a top portion of the balloon contacts the fundus of the uterus;
    inflating the balloon such that operable portions of the peripheral surface of the balloon and the plurality of electrodes contact the patient's endometrium; and
    delivering one or more stimulation signals via the operable portion of the electrodes to the endometrium.

20. The method of claim 19, wherein the operable portions correspond to portions of the balloon and the plurality of electrodes exposed from the sheath.

21. The method of claim 19, further comprising positioning the sheath such that a lip disposed on a distal end of the sheath is seated on the internal os of the cervix.

22. The method of claim 19, further comprising maintaining inoperable portions of the balloon and the plurality of electrodes within the sheath during the inflating and delivering.

23. The method of claim 19, wherein the one or more stimulation signals is one or a combination of RF energy, cryoablation, laser energy, high-intensity focused ultrasound, high-voltage electrical stimulation, and heat.

24. The method of claim 19, further comprising monitoring one or more parameters selected from the group consisting of: tissue temperature, internal balloon pressure, contact, tissue impedance, and humidity.

25. The method of claim 24, wherein the monitoring is performed concurrently with either one or both of the inflating and the delivering.

* * * * *